(12) United States Patent
Topbas et al.

(10) Patent No.: US 11,237,167 B2
(45) Date of Patent: Feb. 1, 2022

(54) LP-PLA2 ASSAYS AND COMPOSITION WITH DETERGENT

(71) Applicant: Cleveland HeartLab, Inc., Cleveland, OH (US)

(72) Inventors: Celalettin Topbas, Wickliffe, OH (US); Cory Bystrom, Beachwood, OH (US)

(73) Assignee: Cleveland Heartlab, Inc., Cleveland, OH (US)

(*) Notice: Subject to any disclaimer, the term of this patent is extended or adjusted under 35 U.S.C. 154(b) by 434 days.

(21) Appl. No.: 15/874,078

(22) Filed: Jan. 18, 2018

(65) Prior Publication Data

US 2018/0209977 A1     Jul. 26, 2018

Related U.S. Application Data

(60) Provisional application No. 62/449,898, filed on Jan. 24, 2017.

(51) Int. Cl.
*G01N 33/573* (2006.01)
*G01N 1/28* (2006.01)

(52) U.S. Cl.
CPC .............. *G01N 33/573* (2013.01); *G01N 1/28* (2013.01); *G01N 2333/92* (2013.01); *G01N 2800/32* (2013.01)

(58) Field of Classification Search
CPC ...................................................... G01N 1/28
See application file for complete search history.

(56) References Cited

FOREIGN PATENT DOCUMENTS

| WO | WO 2014144040 | * | 2/2014 |
| WO | WO 2015/123598 | * | 8/2015 |

OTHER PUBLICATIONS

Goncalves et al., Evidence Supporting a Key Role of Lp-PLA2-Generated Lysophosphatidylcholine in Human Atherosclerotic Plaque Inflammation, Aterioscler. Thromb. Vasc. Biol. 2012; 32: 1505-1512.*
Hough et al., J of Andrology, 1997, 18(5):540-548.*

* cited by examiner

*Primary Examiner* — Bin Shen
(74) *Attorney, Agent, or Firm* — Foley & Lardner LLP

(57) ABSTRACT

Provided herein are methods, systems, and compositions for Lp-PLA2 detection assays that employ amounts of detergent to liberate all or nearly all of the Lp-PLA2 molecules from associated lipoprotein particles. In this regard, the true Lp-PLA2 concentration can be detected in a sample, which correlates better with known Lp-PLA2 activity assays.

14 Claims, 8 Drawing Sheets

A.

B.

LP-PLA2 ASSAYS AND COMPOSITION WITH DETERGENT

The present application claims priority to U.S. Provisionals application 62/449,898 filed Jan. 24, 2017, which is herein incorporated by reference in its entirety.

FIELD OF THE INVENTION

Provided herein are methods, systems, and compositions for Lp-PLA2 detection assays that employ amounts of detergent to liberate all or nearly all of the Lp-PLA2 molecules from associated lipoprotein particles. In this regard, the true Lp-PLA2 concentration can be detected in a sample, which correlates better with known Lp-PLA2 activity assays.

BACKGROUND

Lipoprotein Associated Phospholipase A2 (Lp-PLA2) is a novel biomarker for Cardiovascular Disease. Both the concentration and the activity of Lp-PLA2 have been shown to be associated with risk of coronary heart disease (1). While enzyme linked immunoassays are utilized to quantitate plasma Lp-PLA2 concentration, radiometric and colorimetric assays have been used to measure the activity of this enzyme (2). Even though they report different numeric values there is a strong correlation between different Lp-PLA2 activity methods (2). However Immunoassays, which are used to measure the concentration of Lp-PLA2, do not correlate with activity assays and with one another (1, 3, 4, 5, 6).

SUMMARY OF THE INVENTION

Provided herein are methods, systems, and compositions for Lp-PLA2 detection assays that employ amounts of detergent to liberate all or nearly all of the Lp-PLA2 molecules from associated lipoprotein particles. In this regard, the true Lp-PLA2 concentration can be detected in a sample, which correlates better with known Lp-PLA2 activity assays.

In some embodiments, provided herein are methods of detecting lipoprotein-associated phospholipase A2 (Lp-PLA2) in a sample comprising: a) contacting a sample with a first amount of detergent and Lp-PLA2 binding molecules (e.g., antibodies or binding portions thereof), wherein the sample comprises Lp-PLA2 associated with lipoprotein particles, and wherein the first amount of detergent is sufficient such that: i) at least 95% (e.g., at least 95 . . . 97 . . . 99 . . . 99.9 or 100%) of all of the Lp-PLA2 in the sample that is associated with the lipoprotein particles is liberated from the lipoprotein particles; and/or ii) the ratio of Lp-PLA2 concentration, in ng/ml, to Lp-PLA2 activity, in nmol/min/ml, is at least 12:1, wherein the Lp-PLA2 concentration is as determined in step b), and wherein the Lp-PLA2 activity is determined with an mass spectrometry based activity assay, and wherein the Lp-PLA2 binding molecules bind to Lp-PLA2 to form complexes; and/or iii) the correlation coefficient (r) of Lp-PLA2 concentration to Lp-PLA2 activity is at least 0.9 (e.g., at least 0.9 . . . 0.92 . . . 0.94 . . . 0.96 . . . 0.98 . . . or 1.0), wherein the Lp-PLA2 concentration is as determined in step b), and wherein the Lp-PLA2 activity is determined with a quantitative activity assay, and b) detecting the complexes, thereby determining the Lp-PLA2 concentration in the sample.

In particular embodiments, first amount of the detergent is sufficient that that at least 98% of all of the Lp-PLA2 in the sample that is associated with the lipoprotein particles is liberated from the lipoprotein particles. In other embodiments, the first amount of the detergent is sufficient such that at least 99% of all of the Lp-PLA2 in the sample that is associated with the lipoprotein particles is liberated from the lipoprotein particles. In other embodiments, the first amount of the detergent is sufficient such that at all or substantially all of the Lp-PLA2 in the sample that is associated with the lipoprotein particles is liberated from the lipoprotein particles.

In certain embodiments, the ratio is at least 13:1. In other embodiments, the ratio is at least 14:1. In further embodiments, the ratio is at least 18:1 or wherein the ratio is between 12:1 and 15:1. In some embodiments, the sample is from a patient suspected of having, or diagnosed with, cardiovascular disease. In other embodiments, the sample is selected from the group consisting of: a serum sample, a plasma sample, and a blood sample.

In other embodiments, the detergent is non-ionic, ionic, zwitterionic or chaotropic. In further embodiments, the agent is selected from the group consisting of: Triton X-100, Deoxycholate, sodium dodecyl sulfate, cholate, sarkosyl, DDM, digitonin, tween 20, tween 80, or UREA. In particular embodiments, the Lp-PLA2 binding molecules are selected from the group of: aptamers, antibodies, or antigen-binding portions of antibodies. In some embodiments, the detecting the complexes comprises performing a turbidimetric assay. In certain embodiments, the Lp-PLA2 binding molecules are bound to latex microparticles. In particular embodiments, the detecting the complexes comprises performing an ELISA assay. In certain embodiments, the Lp-PLA2 binding molecules are bound to a well of a multi-well plate.

In some embodiments, provided herein are compositions comprising: a) a sample, wherein the sample is a plasma, serum, or blood sample, and wherein the sample comprises Lp-PLA2 molecules and lipoprotein particles, and b) a first amount of detergent mixed with the sample, wherein the first amount of detergent is sufficient such that 5% or less of the Lp-PLA2 molecules present in the sample are associated with the lipoprotein particles.

In certain embodiments, the compositions further comprise: c) Lp-PLA2 binding molecules. In further embodiments, the Lp-PLA2 binding molecules are selected from the group of: aptamers, antibodies, or antigen-binding portions of antibodies. In additional embodiments, the compositions further comprise latex microparticles, and wherein the Lp-PLA2 binding molecules are bound to the latex microparticles. In particular embodiments, the first amount of detergent is sufficient such that 1-0.1% or less of the Lp-PLA2 molecules present in the sample are associated with the lipoprotein particles. In other embodiments, the sample is from a patient suspected of having, or diagnosed with, cardiovascular disease.

In certain embodiments, provided herein are kits or systems comprising: a) a first amount of detergent mixed with the sample, wherein the first amount of detergent is sufficient such that 5% or less of the Lp-PLA2 molecules present in the sample are associated with the lipoprotein particles; and b) Lp-PLA2 binding molecules. In further embodiments, the first amount of detergent is sufficient such that 0.1-1% or less of the Lp-PLA2 molecules present in the sample are associated with the lipoprotein particles. In additional embodiments, the sample is from a patient suspected of having, or diagnosed with, cardiovascular disease (e.g., atherosclerotic CVD). In some embodiments, the kits and systems further comprise latex microparticles, and wherein the Lp-PLA2 binding molecules are bound to the latex microparticles.

DESCRIPTION OF THE FIGURES

FIG. 8, panel A shows the results with varying concentrations of the exemplary CHL detergent mix (Triton X-100 and Deoxycholate), and FIG. 8, panel B shows the results with varying concentrations of CHAPS detergent.

DEFINITIONS

Figure 1:
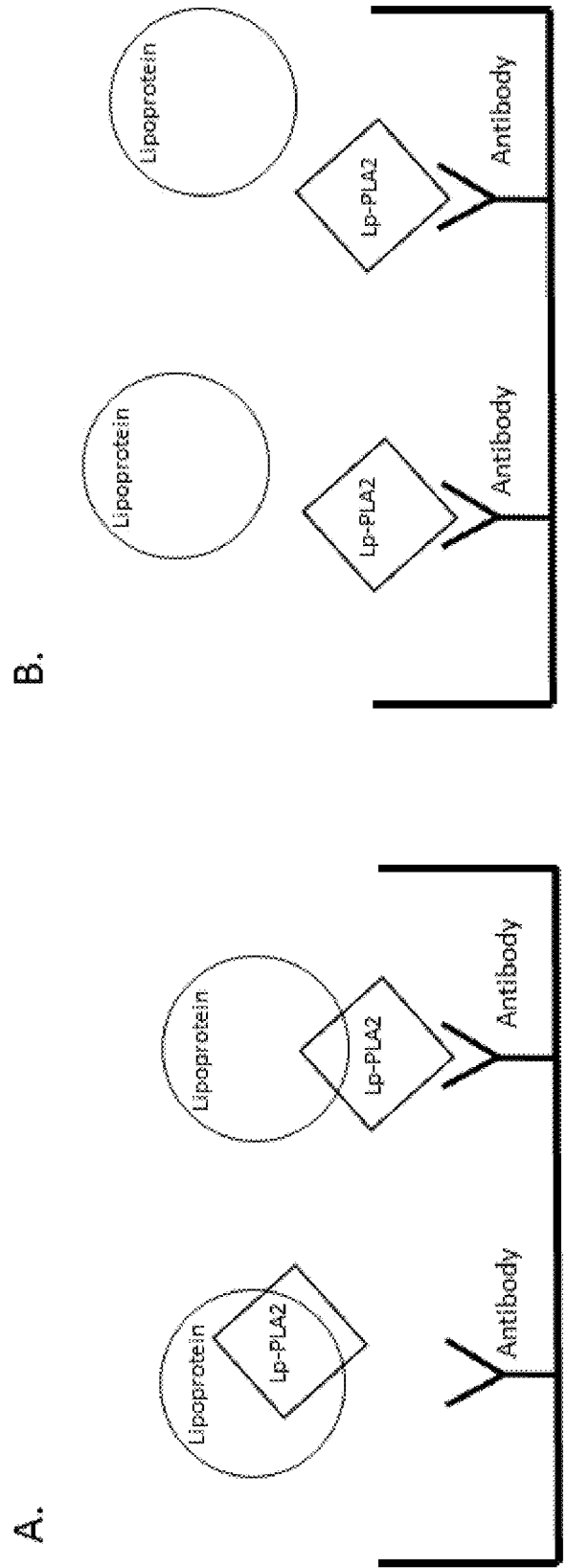
FIG. 1: Lp-PLA2 is associated with Lipoproteins in plasma. The nature of this association may interfere with detection by anti-Lp-PLA2 antibodies on an immune-assay (FIG. 1, Panel A). If the sample is pre-treated with detergents, it disrupts the association between Lp-PLA2 and Lipoproteins and liberates Lp-PLA2. Lp-PLA2 is associated with lipoproteins in serum. Depending on the state of the association Lp-PLA2 epitope may not be available for antibody and cause a partial detection (FIG. 1, Panel A.). Pre-treating serum with detergent liberates Lp-PLA2 and allows full detection (FIG. 1, Panel B).

As used herein, "blood sample" refers to a whole blood sample or a plasma or serum fraction derived therefrom. In certain embodiment, a blood sample refers to a human blood sample such as whole blood or a plasma or serum fraction derived therefrom. In some embodiments, a blood sample refers to a non-human mammalian ("animal") blood sample such as whole blood or a plasma or serum fraction derived therefrom.

As used herein, the term "whole blood" refers to a blood sample that has not been fractionated and contains both cellular and fluid components.

As used herein, "plasma" refers to the fluid, non-cellular component of the whole blood. Depending on the separation method used, plasma may be completely free of cellular components, or may contain various amounts of platelets and/or a small amount of other cellular components. Because plasma includes various clotting factors such as fibrinogen, the term "plasma" is distinguished from "serum" as set forth below.

As used herein, the term "serum" refers to whole mammalian serum, such as, for example, whole human serum, whole serum derived from a test animal, whole serum derived from a pet, whole serum derived from livestock, etc. Further, as used herein, "serum" refers to blood plasma from which clotting factors (e.g., fibrinogen) have been removed.

As used herein, the terms "cardiovascular disease" (CVD) or "cardiovascular disorder" are terms used to classify numerous conditions affecting the heart, heart valves, and vasculature (e.g., veins and arteries) of the body and encompasses diseases and conditions including, but not limited to arteriosclerosis, atherosclerosis, myocardial infarction, acute coronary syndrome, angina, congestive heart failure, aortic aneurysm, aortic dissection, iliac or femoral aneurysm, pulmonary embolism, primary hypertension, atrial fibrillation, stroke, transient ischemic attack, systolic dysfunction, diastolic dysfunction, myocarditis, atrial tachycardia, ventricular fibrillation, endocarditis, arteriopathy, vasculitis, atherosclerotic plaque, vulnerable plaque, acute coronary syndrome, acute ischemic attack, sudden cardiac death, peripheral vascular disease, coronary artery disease (CAD), peripheral artery disease (PAD), and cerebrovascular disease.

As used herein, the phrase "suspected of having CVD" refers to a patient with at least one sign or symptom related to CVD, such as extreme fatigue, constant dizziness or lightheadedness, a fast heart rate (e.g., more than 100 beats per minute at rest), a new irregular heartbeat, chest pain or discomfort during activity that goes away with rest, difficulty breathing during regular activities and rest, a respiratory infection or cough that becomes worse, restlessness or confusion, changes in sleep patterns, and loss of appetite or nausea.

As used herein, the term "atherosclerotic cardiovascular disease" or "disorder" refers to a subset of cardiovascular disease that include atherosclerosis as a component or precursor to the particular type of cardiovascular disease and includes, without limitation, CAD, PAD, cerebrovascular disease. Atherosclerosis is a chronic inflammatory response that occurs in the walls of arterial blood vessels. It involves the formation of atheromatous plaques that can lead to narrowing ("stenosis") of the artery, and can eventually lead to partial or complete closure of the arterial opening and/or plaque ruptures. Thus, atherosclerotic diseases or disorders include the consequences of atheromatous plaque formation and rupture including, without limitation, stenosis or narrowing of arteries, heart failure, aneurysm formation including aortic aneurysm, aortic dissection, and ischemic events such as myocardial infarction and stroke. In certain embodiments, the methods, compositions, and systems disclosed here are used to at least partially diagnose atherosclerotic CVD.

The terms "individual," "host," "subject," and "patient" are used interchangeably herein, and generally refer to a mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos. In some embodiments, the subject is specifically a human subject.

DETAILED DESCRIPTION

Provided herein are methods, systems, and compositions for Lp-PLA2 detection assays that employ amounts of detergent to liberate all or nearly all of the Lp-PLA2 molecules from associated lipoprotein particles. In this regard, the true Lp-PLA2 concentration can be detected in a sample, which correlates better with known Lp-PLA2 activity assays.

Art known Immuno Assay methods were not designed to fully release Lp-PLA2 from its association to lipoproteins. Due to this lack of pre-treatment immuno-assays fail to detect all Lp-PLA2. In the present disclosure, the samples are treated with a detergent or detergent mix and incubated to release Lp-PLA2 from complexes before put into immune assay plate.

The art known PLAC assay does not provide for such detergent treatment to release all or nearly all of the Lp-PLA2 from lipoproteins. As an example, the PLAC assay may be modified with detergent as follows:

Dilute samples with stripped serum (20 uL serum+20 uL stripped serum)
Add 40 uL of the detergent mix (2% Triton X-100, 0.5% Deoxycholate, 20 mM Tris pH 8.0) and vortex.
Incubate at 37° C. for one hour
Dilute calibrators and QCs with the detergent mix (20 uL calibrator+20 uL detergent mix (2% Triton X-100, 0.5% Deoxycholate, 20 mM Tris pH 8.0)) and vortex.
Following the manufacturers protocol put 20 uL diluted calibrators, QC and samples in appropriate wells of the assay plate, and incubate for 10 minutes
Add 200 uL conjugate to all wells and incubate for 3 hours
Aspirate and wash the plate 4× with provided wash buffer.
Add 100 uL TMB reagent and incubate for 20 min in dark.
Add 100 uL stop solution and measure the absorbance at 450 nm with a plate reader.
Apply a quadratic curve fit to standards and calculate Lp-PLA2 concentrations.

In certain embodiments, the increased amounts of detergent used herein allow for the development of immuno-assays with more convenient sample handling and improved sample stability (e.g., longer storage or not having to be frozen).

EXAMPLES

Example 1

Figure 2:
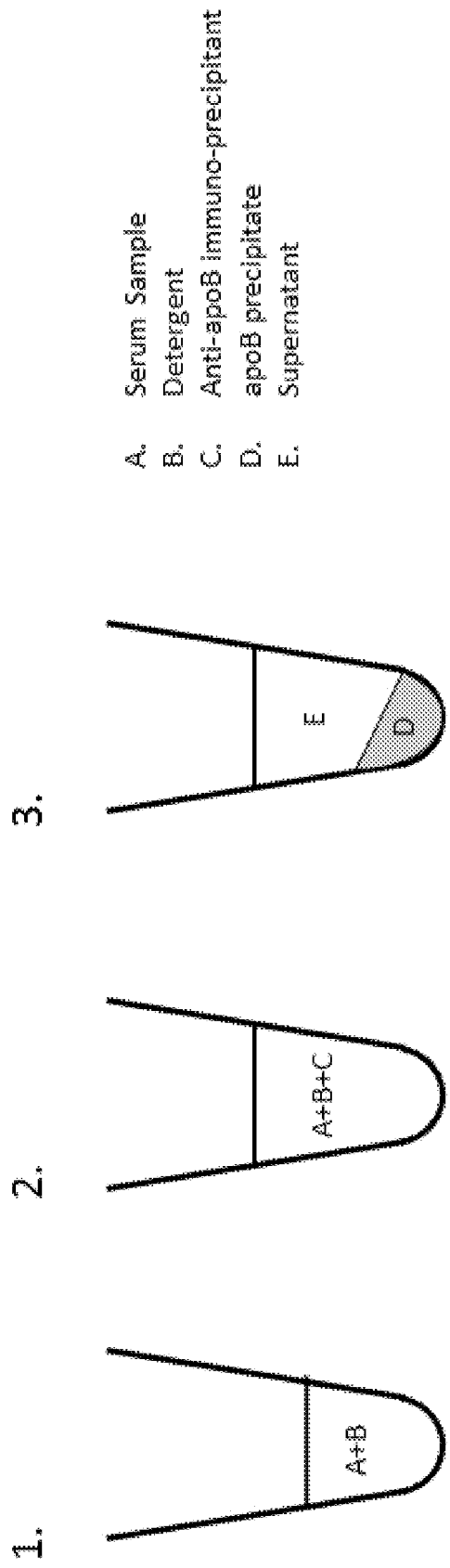
FIG. 2: Sample preparation for Western-Blot analysis. Serum samples were pretreated with a detergent mix (1% Triton X-100, 0.25% Deoxycholate, 20 mM tris pH 8.0), Step 1. Then an anti-apoB immuno-precipitant (LipoSep IP, Sun Diagnostics) is added to this mix, and incubated for 10 minutes to form the apoB precipitant, Step 2. The mix is put into a mini-centrifuge (10 min at 10K g) and separated the apo-B precipitate from the supernatant, Step 3. Lp-PLA2 liberated from LDL particles do not precipitate with apoB and stay in the supernatant.

This example describes testing various detergent combinations with Lp-PLA2 assays. First a combination of detergents (1% Triton X-100, 0.25% Deoxycholate, 20 mM tris pH 8.0) was tested to see if the detergent mix liberates the Lp-PLA2 from its association to lipoproteins in serum. Serum samples were pretreated with a detergent mix (1% Triton X-100, 0.25% Deoxycholate, 20 mM tris pH 8.0), Step 1 (FIG. 2). Then an anti-apoB immuno-precipitant (LipoSep IP, Sun Diagnostics) is added to this mix, and incubated for 10 minutes to form the apoB precipitant, Step 2 (FIG. 2). The mix is put into a mini-centrifuge (10 min at 10K g) and separated the apo-B precipitate from the supernatant, Step 3 (FIG. 2). Lp-PLA2 liberated from LDL particles do not precipitate with apoB and stay in the supernatant.

Figure 3:
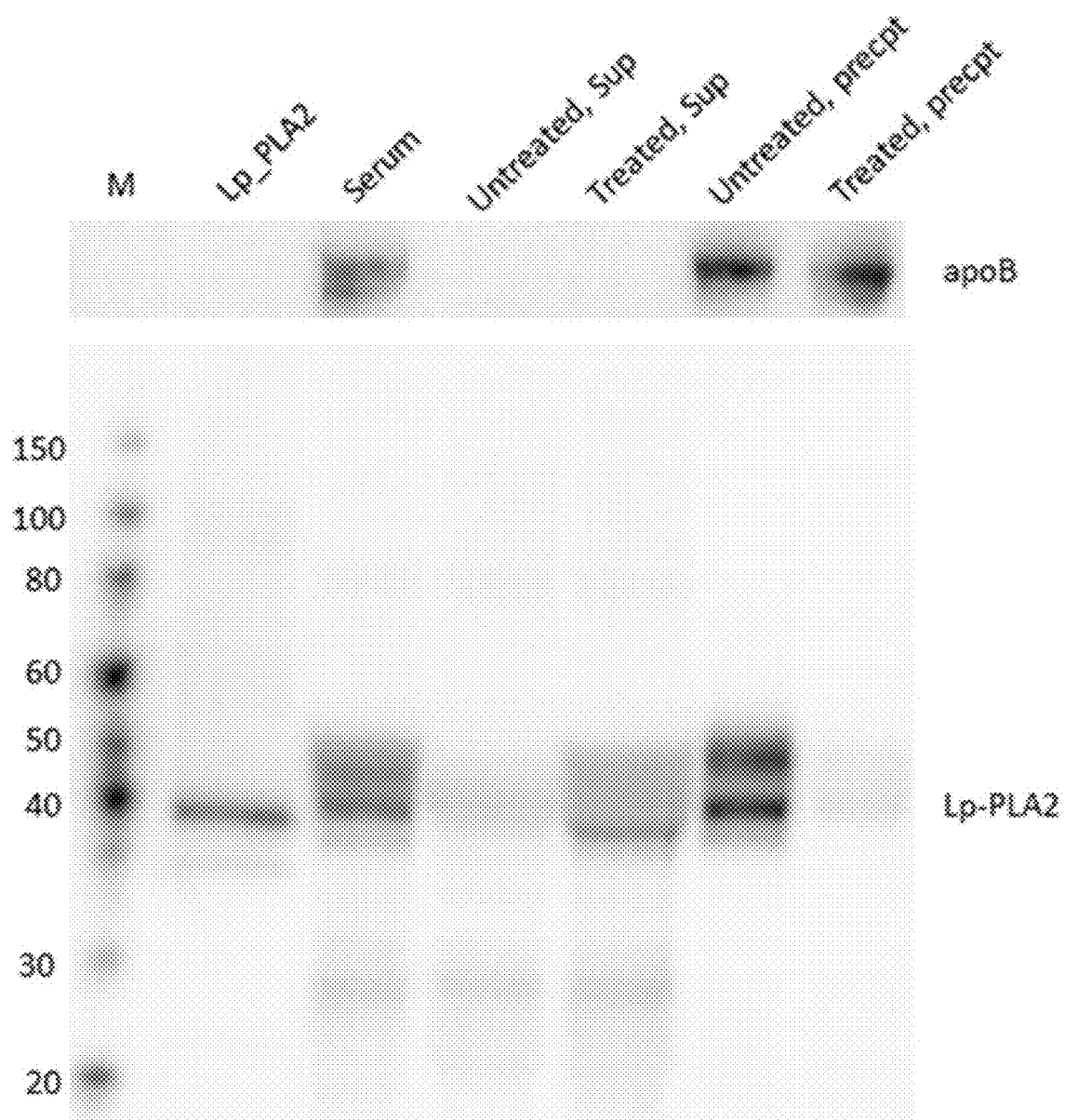
FIG. 3 shows a Western blot that shows that detergent mix liberates Lp-PLA2 from its complexes with lipoproteins. Proteins in the supernatant or precipitant of apoB immuno precipitation were separated by gradient (4-12% Bis-Tris) reducing SDS-PAGE. Bottom panel, Western Blot membrane probed with anti-Lp-PLA2 antibody, top panel, with anti-apoB antibody. Molecular mass marker is indicated. Serum samples with detergent treatment were immuno-precipitated with anti-apoB antibodies (FIG. 2) and compared with untreated samples. Upon precipitation, supernatant and precipitant proteins were separated on a gradient SDS-PAGE and transferred to a western blot membrane. The membrane was then probed with an anti-Lp-PLA2 antibody (Cayman Chemical), stripped and re-probed with anti-apoB (abcam).

Detergent mix liberates Lp-PLA2 from its complexes with lipoproteins. Proteins in the supernatant or precipitant of apoB immuno precipitation were separated by gradient (4-12% Bis-Tris) reducing SDS-PAGE. This is shown in the Western Blot in FIG. 3. The bottom panel of FIG. 3 shows a Western Blot membrane probed with anti-Lp-PLA2 antibody, and the top panel of FIG. 3, shows a Western Blot membrane probed with anti-apoB antibody. Molecular mass marker is indicated. Serum samples with detergent treatment were immuno-precipitated with anti-apoB antibodies (FIG. 2) and compared with untreated samples. Upon precipitation, supernatant and precipitant proteins were separated on a gradient SDS-PAGE and transferred to a Western blot membrane. The membrane was then probed with an anti-Lp-PLA2 antibody (Cayman Chemical), stripped and re-probed with anti-apoB (abcam).

Visual inspection of the Western blot membrane reveals that most of the Lp-PLA2 is associated with LDL and precipitates in apoB-IP, while relatively small amount resides in the supernatant. However, in the detergent treated sample, most of the Lp-PLA2 remains in the supernatant and hardly any in the precipitate, suggesting Lp-PLA2 is liberated from LDL particles.

Figure 4:
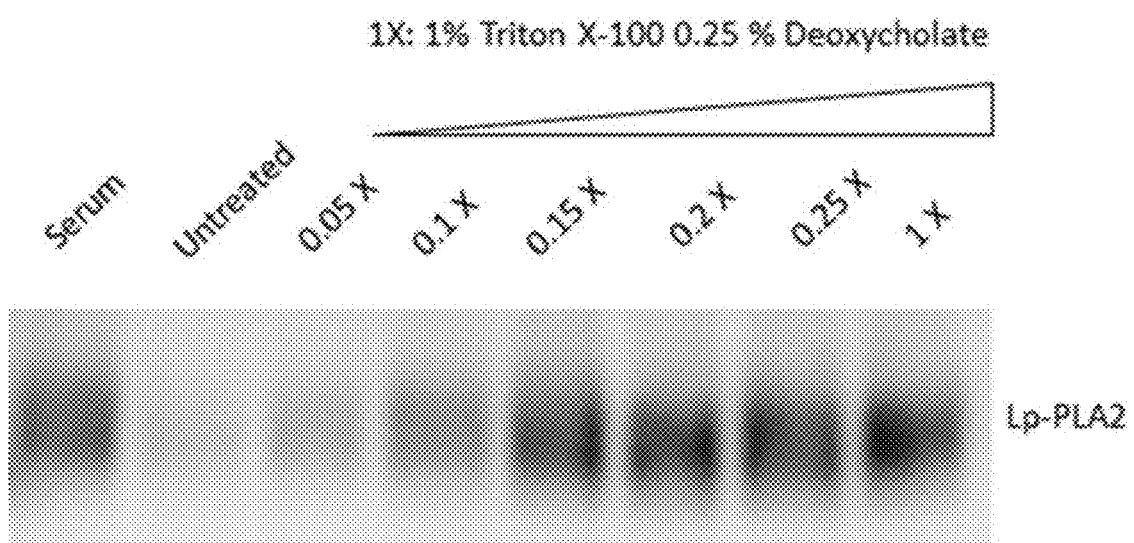
FIG. 4: The effect of detergent concentration on Lp-PLA2 liberation in treated serum is shown. Serum samples treated with increasing concentration of detergents and immuno-precipitated with anti-apoB antibodies (FIG. 2) and compared with untreated sample. Upon precipitation, supernatant proteins were separated on a gradient SDS-PAGE (4-12% Bis-Tris) and transferred to a western blot membrane. The membrane was then probed with an anti-Lp-PLA2 antibody (Cayman Chemical).

Next, the effect of detergent concentration on Lp-PLA2 liberation was investigated. Serum samples are incubated with increasing concentrations of the detergent mix from no detergent to final 1% Triton X-100, 0.25% Deoxycholate (1× concentration) as shown in FIG. 4. FIG. 4 shows the effect of detergent concentration on Lp-PLA2 liberation in treated serum. Serum samples treated with increasing concentration of detergents and immuno-precipitated with anti-apoB antibodies (FIG. 2) and compared with untreated sample. Upon precipitation, supernatant proteins were separated on a gradient SDS-PAGE (4-12% Bis-Tris) and transferred to a western blot membrane. The membrane was then probed with an anti-Lp-PLA2 antibody (Cayman Chemical).

The western blot experiment shows that more Lp-PLA2 is liberated with increasing concentration of detergent mix and Lp-PLA2 stays in the supernatant of apoB-IP. The small amount of Lp-PLA2 in the untreated serum supernatant is possibly HDL bound Lp-PLA2 which doesn't precipitate in apoB IP.

Figure 5:
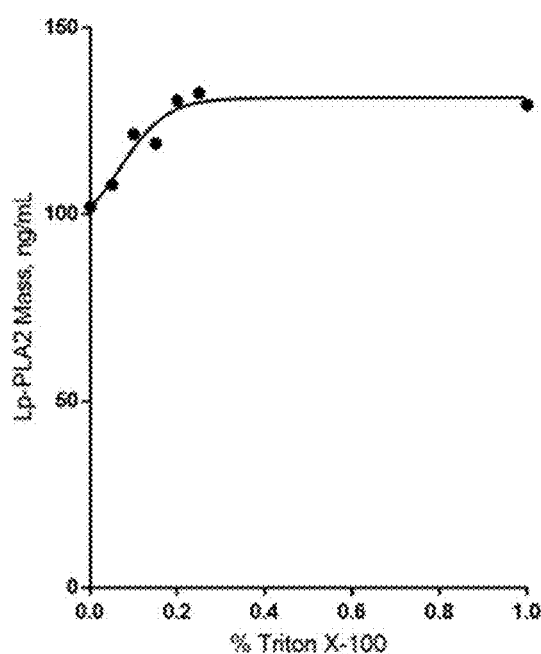
FIG. 5 shows the effect of detergent concentration on Lp-PLA2 Mass detection on an immunoassay. Serum samples were incubated with increasing concentrations of Triton X-100 (0, 0.05, 0.1, 0.15, 0.2, 0.25 and 1%) or Deoxycholate (0, 0.05, 0.1, 0.15, 0.2, 0.25 and 0.5%) and assayed for their Lp_PLA2 concentration (Human Lp-PLA2 Quantikine ELISA kit, R&D Systems), panel A and panel B respectively.
Figure 5:
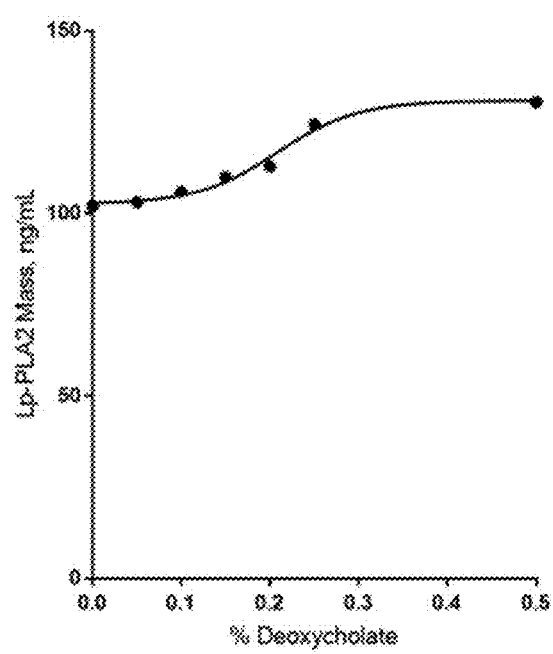

Following on this finding, increasing detergent concentration on Lp-PLA2 mass detection was tested in an immuno assay (Human Lp-PLA2 Quantikine ELISA Kit, R&D Systems). Serum samples are incubated with increasing concentrations of Triton X-100 or Deoxycholate and assayed for Lp-PLA2 concentration (FIG. 5). FIG. 5 shows the effect of detergent concentration on Lp-PLA2 Mass detection on an immunoassay. Serum samples were incubated with increasing concentrations of Triton X-100 (0, 0.05, 0.1, 0.15, 0.2, 0.25 and 1%) or Deoxycholate (0, 0.05, 0.1, 0.15, 0.2, 0.25 and 0.5%) and assayed for their Lp_PLA2 concentration (Human Lp-PLA2 Quantikine ELISA kit, R&D Systems), panel A and B respectively. More Lp-PLA2 is detected with increasing concentration of detergents consistent with the observation in Western Blot experiment. The plateau suggest that all Lp-PLA2 is liberated after a certain detergent concentration.

Figure 6:
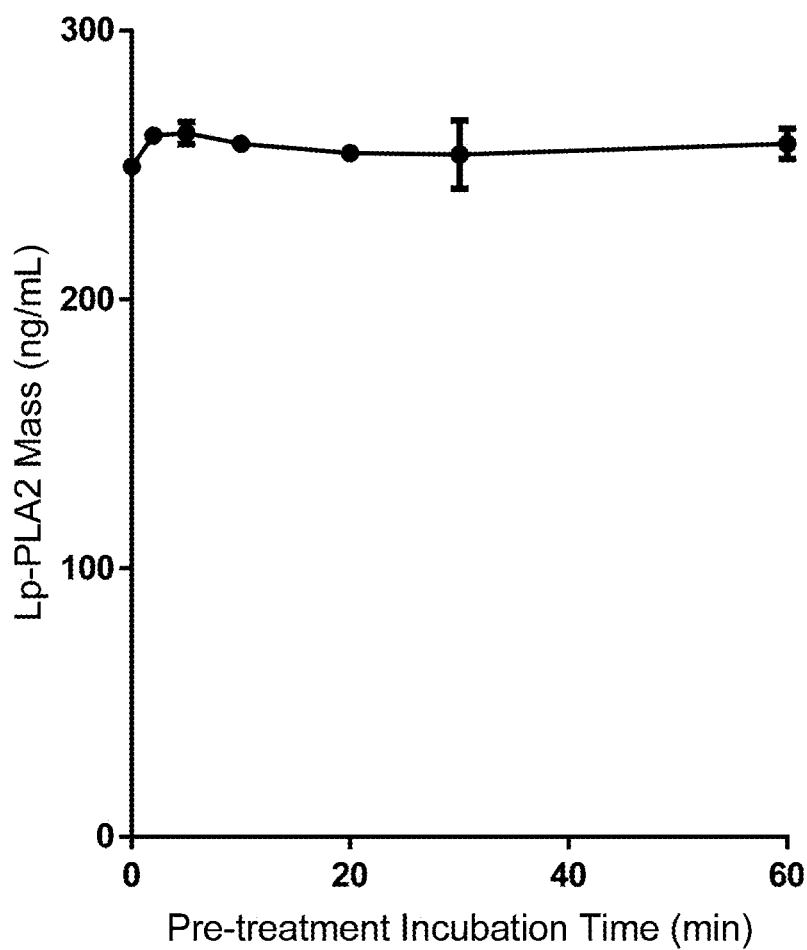
FIG. 6 shows the effect of pre-treatment incubation time on Lp-PLA2 liberation. Serum samples were pre-treated with a detergent mix (1% Triton X-100, 0.25% Deoxycholate, 20 mM tris pH 8.0) and incubated at various times. The liberated Lp-PLA2 in serum is separated from LDL-bound Lp-PLA2 with an apoB immuno-precipitation (FIG. 2). Supernatant of the treated samples were assayed for their Lp-PLA2 concentration (Human Lp-PLA2 Quantikine ELISA kit, R&D Systems).

A time-dependent experiment is performed to assess the effect of incubation time on liberation of Lp-PLA2 during the pre-treatment of samples. Serum samples are incubated with the detergent mix (1% Triton X-100, 0.25% Deoxycholate, 20 mM Tris pH 8.0) and incubated at various times (0, 2, 5, 10, 20, 30, and 60 minutes). Then the samples are mixed with apoB Immuno-precipitant and the supernatant is assayed for Lp-PLA2 concentration (FIG. 6). FIG. 6 shows the effect of pre-treatment incubation time on Lp-PLA2 liberation. Serum samples were pre-treated with a detergent mix (1% Triton X-100, 0.25% Deoxycholate, 20 mM tris pH 8.0) and incubated at various times. The liberated Lp-PLA2 in serum is separated from LDL-bound Lp-PLA2 with an apoB immuno-precipitation (FIG. 2). Supernatant of the treated samples were assayed for their Lp-PLA2 concentration (Human Lp-PLA2 Quantikine ELISA kit, R&D Systems). The incubation time experiment shows that all Lp-PLA2 is liberated upon mixing the sample with detergents.

Finally, Lp-PLA2 activity was tested in 79 samples with an LDT assay (Table 1). To assess the correlation of activity to mass, Lp-PLA2 mass was measured with two immunoassays: original PLAC-mass assay and adjusted PLAC-mass assay.

TABLE 1

| Sample # | PLAC (original)* Mass ng/mL | PLAC (detergent)** Mass ng/mL | Activity nmol/min/mL | Sample # | PLAC (original) Mass ng/mL | PLAC (detergent) Mass ng/mL | Activity nmol/min/mL |
|---|---|---|---|---|---|---|---|
| 1 | 228 | 763 | 49 | 41 | 143 | 528 | 37 |
| 2 | 376 | 999 | 67 | 42 | 195 | 1083 | 75 |
| 3 | 184 | 715 | 46 | 43 | 306 | 871 | 57 |
| 4 | 201 | 600 | 41 | 44 | 212 | 856 | 64 |
| 5 | 167 | 495 | 33 | 45 | 160 | 1024 | 67 |
| 6 | 79 | 297 | 22 | 46 | 139 | 776 | 51 |
| 7 | 51 | 335 | 31 | 47 | 206 | 1304 | 81 |
| 8 | 165 | 609 | 45 | 48 | 136 | 545 | 41 |
| 9 | 324 | 1098 | 69 | 49 | 137 | 548 | 39 |
| 10 | 162 | 604 | 46 | 50 | 191 | 679 | 38 |
| 11 | 222 | 701 | 44 | 51 | 187 | 561 | 44 |
| 12 | 162 | 1101 | 75 | 52 | 255 | 502 | 27 |
| 13 | 223 | 581 | 44 | 53 | 137 | 618 | 45 |
| 14 | 174 | 1000 | 66 | 54 | 176 | 592 | 44 |
| 15 | 144 | 613 | 42 | 55 | 216 | 761 | 55 |
| 16 | 431 | 1238 | 74 | 56 | 247 | 664 | 38 |
| 17 | 168 | 740 | 50 | 57 | 209 | 878 | 58 |
| 18 | 425 | 898 | 67 | 58 | 190 | 692 | 51 |
| 19 | 105 | 370 | 25 | 59 | 177 | 827 | 61 |
| 20 | 138 | 546 | 42 | 60 | 270 | 638 | 41 |
| 21 | 233 | 1102 | 71 | 61 | 217 | 600 | 42 |
| 22 | 126 | 648 | 47 | 62 | 157 | 680 | 46 |
| 23 | 168 | 348 | 23 | 63 | 180 | 1340 | 56 |
| 24 | 168 | 519 | 33 | 64 | 169 | 1036 | 57 |
| 25 | 185 | 429 | 36 | 65 | 261 | 702 | 53 |
| 26 | 173 | 593 | 43 | 66 | 203 | 594 | 42 |
| 27 | 168 | 741 | 53 | 67 | 188 | 600 | 44 |
| 28 | 200 | 660 | 45 | 68 | 198 | 902 | 62 |
| 29 | 181 | 586 | 42 | 69 | 79 | 539 | 41 |
| 30 | 160 | 561 | 37 | 70 | 219 | 847 | 56 |
| 31 | 130 | 618 | 41 | 71 | 245 | 1387 | 86 |
| 32 | 166 | 655 | 45 | 72 | 243 | 1161 | 80 |
| 33 | 159 | 801 | 51 | 73 | 227 | 672 | 46 |
| 34 | 148 | 1035 | 69 | 74 | 239 | 751 | 46 |
| 35 | 131 | 684 | 42 | 75 | 186 | 963 | 63 |
| 36 | 157 | 1155 | 73 | 76 | 231 | 850 | 60 |
| 37 | 210 | 853 | 57 | 77 | 129 | 360 | 26 |
| 38 | 157 | 484 | 33 | 78 | 259 | 1123 | 73 |
| 39 | 181 | 725 | 49 | 79 | 157 | 763 | 54 |
| 40 | 140 | 520 | 37 | | | | |

Figure 7:
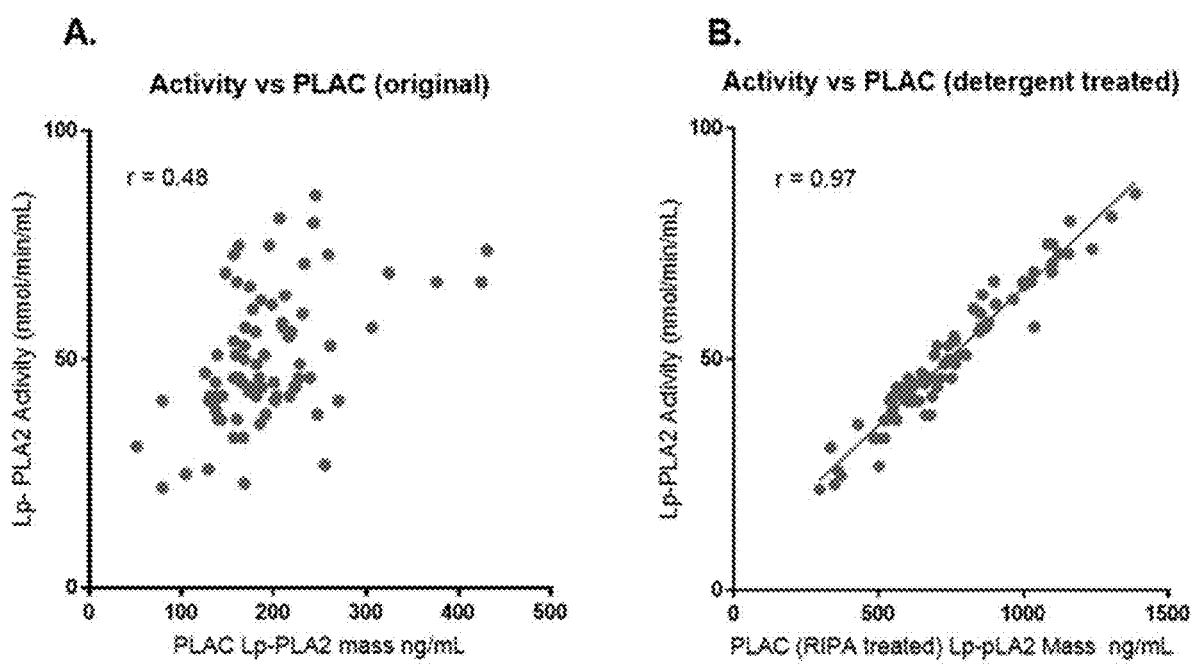
FIG. 7: Panel A shows a graph showing there is a poor correlation between the Lp-PLA2 activity and mass if the original immuno-assay method applied (r=0.48). However pre-treating samples with detergents and liberating Lp-PLA2 from lipoprotein complexes yields higher mass values and the results correlate better with the activity assay (r=0.97) (FIG. 7, panel B.)

*PLAC (original) Mass: PLAC-Mass assay without any alteration
**PLAC (detergent) Mass: PLAC-Mass assay with a pre-treatment of the samples with the detergent mix As seen in the graph in FIG. 7, Panel A, there is a poor correlation between the Lp-PLA2 activity and mass if the original immuno-assay method applied (r=0.48). However pre-treating samples with detergents and liberating Lp-PLA2 from lipoprotein complexes yields higher mass values and the results correlate better with the activity assay (r=0.97) (FIG. 7, Panel B)

Example 2

Comparison to 0-40 mM CHAPS Detergent

The Caslake et al. reference (Atherosclerosis, 150:413-419, 2000) describes an Lp-PLA2 immunoassay that employed 20 mM CHAPS detergent. This Example provides a comparison between certain exemplary detergent conditions from the present application ("CHL detergent") vs. the 20 mM CHAPS from Caslake et al. This Example further tests the range of 0-40 mM CHAPS for comparison purposes.

Figure 8:
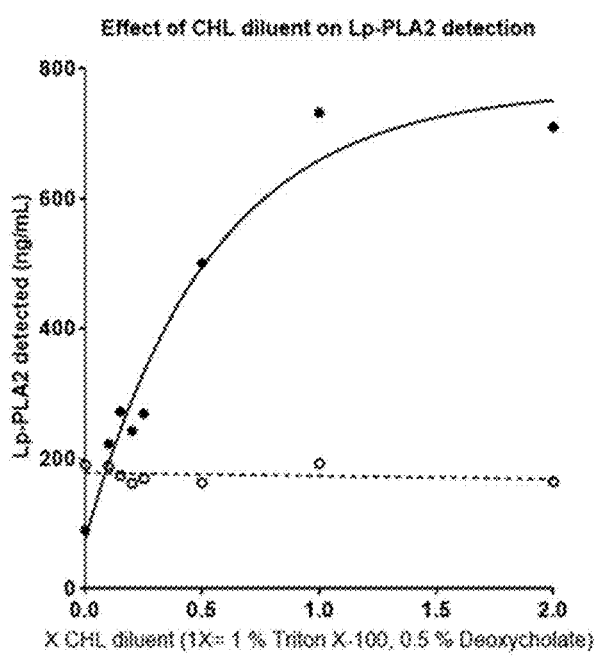
FIG. 8 shows the effect of detergent treatment on Lp-PLA2 detection by PLAC immunoassay.
Figure 8:
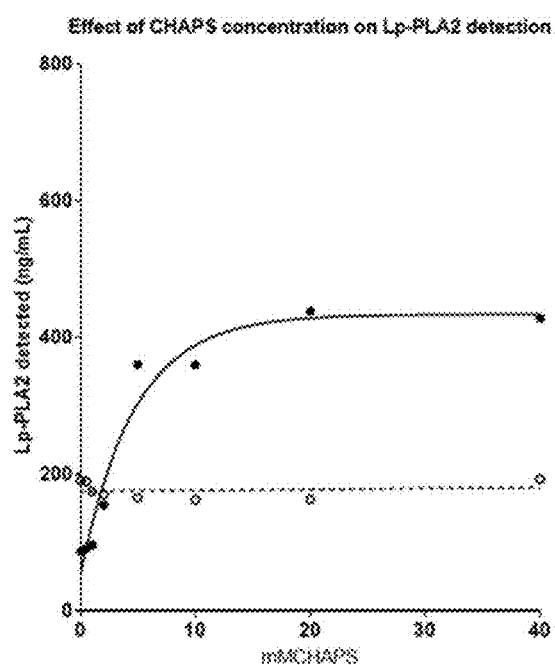

The various concentrations of CHL detergent (Triton X-100 and Deoxycholate) and CHAPS detergent (0-40 mM) are as shown on the x-axis in FIG. 8, Panel A and Panel B respectively. These detergents were mixed with a serum sample and tested in a commercial PLAC kit Lp-PLA2 immunonassay to assess/compare their effect on Lp-PLA2 immunodetection.

FIG. 8 shows the effect of detergent treatment on Lp-PLA2 detection by a commercial PLAC immunoassay. A serum sample is treated with increasing concentrations of detergent and assayed for Lp-PLA2 concentration, solid line. Note that Lp-PLA2 is bound to lipoproteins in serum. For control, lipoprotein free, recombinant Lp-PLA2 is assayed in parallel, dashed line. More Lp-PLA2 is detected by increasing concentration of detergents and a plateau is reached after certain concentration of detergent, while the detergents seems to have no effect on the detection of the lipoprotein free recombinant Lp-PLA2.

The treatment of serum samples with the exemplary CHL detergent mix (Triton X-100 and Deoxycholate) increases the Lp-PLA2 immunodetection by a factor of 8. On the other hand, treating same samples with CHAPS increases only 4 fold. It is estimated, based on these results, that, for this particular serum sample, the Lp-PLA2 release is 59% for the CHAPS sample (including at the 20 mM CHAPS in the Caslake et al. reference). It is also estimated that greater than 95% of the Lp-PLA2 is released for the exemplary CHL sample diluent.

REFERENCES

1. Lp-pla, T. & Collaboration, S. Lipoprotein-associated phospholipase A 2 and risk of coronary disease, stroke, and mortality: collaborative analysis of 32 prospective studies. 375, (2010).
2. Stafforini, D. M. & McIntyre, T. M. Determination of phospholipase activity of PAF acetylhydrolase. Free Radic. Biol. Med. 59, 100-107 (2013).
3. Mcconnell, J. P. & Jaffe, A. S. Variability of Lipoprotein-Associated Phospholipase A2 Measurements. (2007). doi: 10.1373/clinchem. 2007.102160
4. Nelson, J. J., Persson, M., Ake, J.-& Hedblad, B. The epidemiology of Lp-PLA 2: Distribution and correlation with cardiovascular risk factors in a population-based cohort. 190, 388-396 (2007).
5. Trischler, G. & Loewel, H. Variability of Serial Lipoprotein-Associated Phospholipase A 2 Measurements in Post—Myocardial Infarction Patients: Results from the AIRGENE Study Center Augsburg METHODS: CONCLUSIONS: 130, (2008).
6. Donoghue, M. O. et al. Lipoprotein-Associated Phospholipase A 2 and Its Association With Cardiovascular Outcomes in Patients With Acute Coronary Syndromes in the PROVE IT-TIMI 22 (PRavastatin Or atorVastatin Evaluation and Infection Therapy—Thrombolysis In Myocardial Infarction) Trial. 22, (2006).
7. Donato, L. J., Meeusen, J. W., Callanan, H., Saenger, A. K. & Jaffe, A. S. Advantages of the lipoprotein-associated phospholipase A2 activity assay. Clin. Biochem. 49, 172-175 (2016).

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of detecting lipoprotein-associated phospholipase A2 (Lp-PLA2) in a sample comprising:
    a) contacting a sample with a first amount of a detergent mix and Lp-PLA2 binding molecules,
    wherein said detergent mix comprises two or more detergents,
    wherein said detergent is not CHAPS,
    wherein said sample comprises Lp-PLA2 associated with lipoprotein particles,
    wherein said first amount of the detergent mix is sufficient such that at least 95% of all of said Lp-PLA2 in said sample that is associated with said lipoprotein particles is liberated from said lipoprotein particles, and
    wherein said Lp-PLA2 binding molecules bind to Lp-PLA2 to form complexes; and
    b) detecting said complexes, thereby determining said Lp-PLA2 concentration in said sample.

2. The method of claim 1, wherein said first amount of the detergent mix is sufficient such that at least 98% of all of said Lp-PLA2 in said sample that is associated with said lipoprotein particles is liberated from said lipoprotein particles.

3. The method of claim 1, wherein a ratio of Lp-PLA2 concentration, in ng/ml, to Lp-PLA2 activity, in nmol/min/ml, is at least 12:1, and wherein said Lp-PLA2 activity is determined with a mass-spectrometry based activity assay.

4. The method of claim 3, wherein said ratio is at least 13:1.

5. The method of claim 1, wherein said sample is from a patient suspected of having, or diagnosed with, cardiovascular disease.

6. The method of claim 1, wherein said sample is selected from the group consisting of: a serum sample, a plasma sample, and a blood sample.

7. The method of claim 1, wherein said detergent mix comprises at least an non-ionic detergent.

8. The method of claim 1, wherein said detergent mix comprises at least a ionic detergent.

9. The method of claim 1, wherein said detergent mix comprises at least a zwitterionic or a chaotropic detergent.

10. The method of claim 1, wherein said detergent mix comprises at least one detergent selected from the group consisting of: Triton X-100, Deoxycholate, sodium dodecyl sulfate, cholate, sarkosyl, n-Dodecyl β-D-maltoside (DDM), digitonin, tween 20, tween 80, and urea.

11. The method of claim 1, wherein said Lp-PLA2 binding molecules are selected from the group of: aptamers, antibodies, and antigen-binding portions of antibodies.

12. The method of claim 1, wherein the concentration of said first amount of the detergent mix is between 0.05% to 2%.

13. The method of claim 12, wherein the concentration of said first amount of the detergent mix is between 0.05% to 1%.

14. The method of claim 1, wherein said two or more detergents are selected from the group consisting of: Triton X-100, Deoxycholate, sodium dodecyl sulfate, cholate, sarkosyl, DDM, digitonin, tween 20, tween 80, and urea.

* * * * *